United States Patent
Houge et al.

(10) Patent No.: US 6,577,970 B2
(45) Date of Patent: Jun. 10, 2003

(54) METHOD OF DETERMINING A CRYSTALLOGRAPHIC QUALITY OF A MATERIAL LOCATED ON A SUBSTRATE

(75) Inventors: Erik C. Houge, Orlando, FL (US); John M. McIntosh, Orlando, FL (US); Larry E. Plew, St. Cloud, FL (US); Fred A. Stevie, Orlando, FL (US); Catherine Vartuli, Windermere, FL (US)

(73) Assignee: Agere Systems Inc., Allentown, PA (US)

( * ) Notice: Subject to any disclaimer, the term of this patent is extended or adjusted under 35 U.S.C. 154(b) by 64 days.

(21) Appl. No.: 09/801,455

(22) Filed: Mar. 8, 2001

(65) Prior Publication Data

US 2002/0128789 A1 Sep. 12, 2002

(51) Int. Cl.$^7$ ................................................. G01N 37/00
(52) U.S. Cl. .......................................... 702/81; 702/150
(58) Field of Search ................................. 117/200, 201, 117/902, 69, 85, 86; 438/973; 702/81, 82

(56) References Cited

U.S. PATENT DOCUMENTS

| | | | | |
|---|---|---|---|---|
| 5,016,266 A | * | 5/1991 | Meurtin | 378/73 |
| 5,049,816 A | * | 9/1991 | Moslehi | 324/158 D |
| 5,466,934 A | * | 11/1995 | Adams et al. | 250/307 |
| 5,557,104 A | * | 9/1996 | Field et al. | 250/307 |
| 5,832,138 A | | 11/1998 | Nakanishi et al. | |
| 6,320,655 B1 | * | 11/2001 | Matsushita et al. | 356/237.2 |
| 6,330,354 B1 | * | 12/2001 | Companion et al. | 382/150 |

OTHER PUBLICATIONS

Carver, G; Moore, R; Trapp, K; Kahora, P; Stevie, F; "Detection of Compositional non–Uniformities in InP:Fe Via Spatially Photoluminescence and Secondary Ion Mass Spectrometry"; 2nd Intn'l Conf on Indium Phosphide and Related Materials; 1990; pp. 428–434.*

Maruo, K; Yamaguchi, T; Ichikawa, M; Shibata, T; Ohmi, T; "Automatic Defects Separation form Background LSI Patterns Using Advanced Image Processing Techniques", IEEE Intn'l Symposium on Semiconductor Manufacturing Conference Proceedings; 1997; pp. E–61–E64.*

Aghajan, H K; Kailath, T; "Sensor Array Processing Tecniques for Super Resolution Multi–Line and Straight Edge Detection", IEEE Transactions on Image Processing; vol. 2, Issue 4; 1993; pp. 454–465.*

Aghajan, H K; Kailath, T; "Slide: Subspace–Based Line Detection";IEEE International Conference on Acoustics, Speech and Signal Processing; vol. 5; 1993; pp. 89–92.*

Yue, H H; Qin, S J; Markle, R J; Nauert, C; Gatto, M; "Fault Detection of Plasma Etchers Using Optical Emission Spectra", IEEE Transactions on Semiconductor Manufacturing; vol. 13 Issue 3; 2000; pp. 374–385.*

* cited by examiner

Primary Examiner—John Barlow
Assistant Examiner—Douglas N Washburn (57) ABSTRACT

The present invention provides a method of determining a crystallographic quality of a material located on a substrate. The method includes determining a set of crystallographic solutions for an unknown crystallographic orientation, and subsequently comparing the set of crystallographic solutions to adjacent known crystallographic orientations to determine the unknown crystallographic orientation. In a preferred embodiment, the set of crystallographic solutions may be a rank of crystallographic solutions which may represent the most probable crystallographic orientations. The rank of crystallographic solutions, in an alternative embodiment, may be represented by a vote, a fit and a confidence index.

20 Claims, 8 Drawing Sheets

|   | 1 | 2 | 3 | 4 | 5 | 6 | 7 | 8 | 9 | 10 | 11 |
|---|---|---|---|---|---|---|---|---|---|----|----|
| 1 | X |   | X |   |   |   |   |   |   |    |    |
| 2 |   | X | X |   |   |   |   |   |   |    |    |
| 3 |   | X | X |   |   |   |   |   |   |    |    |
| 4 |   |   | X | X |   |   |   |   |   |    |    |
| 5 |   | X | X | X |   |   |   |   |   |    |    |
| 6 |   |   | X |   | X |   |   |   |   |    |    |
| 7 |   |   | X |   |   | X |   |   |   |    |    |
| 8 |   |   | X |   |   |   | X |   |   |    |    |
| 9 |   |   | X |   |   |   |   | X |   |    |    |
| 10|   |   | X |   |   |   |   |   | X |    |    |
| 11|   |   | X |   |   |   |   |   |   | X  |    |
| 12|   |   | X |   |   |   |   |   |   |    | X  |
| Σ | 2 | 4 | 10| 2 | 1 | 1 | 1 | 1 | 1 | 1  | 1  |

Indexing Solutions (rows) / Band Triplets (columns)

METHOD OF DETERMINING A CRYSTALLOGRAPHIC QUALITY OF A MATERIAL LOCATED ON A SUBSTRATE

TECHNICAL FIELD OF THE INVENTION

The present invention is directed, in general, to materials manufacturing and, more specifically, to a method of determining a crystallographic quality of a material located on a substrate.

BACKGROUND OF THE INVENTION

The advance of the technology of multilevel metal oxide semiconductor (MOS) devices has evolved immensely as the MOS industry strives for faster and more reliable MOS devices. Currently, there is a drive to transition from well-established aluminum metallization, tungsten interconnects, and titanium and titanium nitride barrier layers to copper and its associated materials. For the process of multilevel metallization, the crystallographic nature of the metallization and the nucleation of grain size and structure will have an increasing effect on the quality and yield of the products that are produced. Typically, aluminum deposits via chemical vapor deposition along a well-established fiber texture defined by its {111} plane of atoms. In contrast, copper and the new barrier materials do not have the same baseline orientation as does the aluminum, and therefore might have orientation problems, and more importantly, electromigration (EM) problems that arise from the abnormal grain orientations. As a result, there is a need to be able to accurately discern grain morphology and orientation, such that high quality MOS devices may be manufactured.

Electron Backscatter Kikuchi Diffraction (BKD) has become a viable way to discern both the grain size, crystallographic orientation, and phase determination of materials common to the processing of semiconductors. The Electron Backscatter Kikuchi Diffraction method analyzes collections of backscattering Kikuchi diffraction patterns, therefore, it combines the advantages of point orientation in transmission electron microscope (TEM) with morphological information over a large enough area to provide statistical relevance. The Electron Backscattering Kikuchi Diffraction method has gained wide acceptance, because the broad information about the structure at an atomic crystallographic level cannot easily be discerned by the other techniques commonly known in the art.

However, the Electron Backscatter Kikuchi Diffraction method has problems. One of such problems, is the Electron Backscatter Kikuchi Diffraction method's inability to accurately discern between two adjacent grain structures which are misaligned with a rotation angle of greater than about five degrees. When the grain size of the material being subjected to the Electron Backscatter Kikuchi Diffraction method is on the same order as the spread of the backscattered electron intensity reflection by the incident electron beam and the size of the interaction volume of the diffraction contains a grain boundary, overlapping patterns are generally more discernable. For the transition from well-established aluminum metallization, tungsten interconnects, and titanium and titanium nitride barrier layers, this poses a real problem. Of the barrier layers, titanium nitride, titanium, cobalt silicide, tantalum nitride and others have grain structures that are approaching the size of the area of backscattered electron intensity. For copper interconnects, sigma three twinning creates the same effective change in lattice orientation, thereby creating a misidentification with the boundaries and twin boundaries. These misidentifications then prevent the Electron Backscatter Kikuchi Diffraction method from accurately detecting smaller off axis grain nucleations out of the boundary structure, from the misidentification of overlapping grain structures.

Currently, a ranking scheme is conducted to approximate which grain orientation solution is detected most often for overlapping grain boundaries. The solution that is detected the most times is then determined to be the correct solution. The problem with the ranking scheme is that it does not always provide the correct solution of the grain orientation. For example, it is common for the solution of the grain orientation to be inconsistent with the grain orientations available in the material being tested. Furthermore, the ranking scheme uses a finite number of test plots, which may provide room for statistical error.

Accordingly, what is needed in the art is a method of determining a crystallographic quality of a material located on a substrate, even though overlapping crystallographic patterns may be present, that does not experience the inaccuracies present in the prior art methods.

SUMMARY OF THE INVENTION

To address the above-discussed deficiencies of the prior art, the present invention provides a method of determining a crystallographic quality of a material located on a substrate. The method includes determining a set of crystallographic solutions for an unknown crystallographic orientation, and subsequently comparing the set of crystallographic solutions to adjacent known crystallographic orientations, to determine the unknown crystallographic orientation. In a preferred embodiment, the set of crystallographic solutions may be a rank of crystallographic solutions which may represent the most probable crystallographic orientations. The rank of crystallographic solutions, in an alternative embodiment, may be represented by a vote, a fit and a confidence index.

The above disclosed method, in contrast to prior art methods, is substantially able to accurately determine the crystallographic orientation of two overlapping Kikuchi band formation patterns. Since the set of crystallographic solutions is carried forward until two adjacent known crystallographic orientations have been determined, a more accurate determination of the unknown crystallographic orientation may be found.

The foregoing has outlined, rather broadly, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention in its broadest form.

BRIEF DESCRIPTION OF THE DRAWINGS

The invention is best understood from the following detailed description when read with the accompanying FIGURES. It is emphasized that in accordance with the standard practice in the semiconductor industry, various features are not drawn to scale. In fact, the dimensions of the various features may be arbitrarily increased or reduced for clarity of discussion. Reference is now made to the following descriptions taken in conjunction with the accompanying drawings, in which.

DETAILED DESCRIPTION

Figure 1:
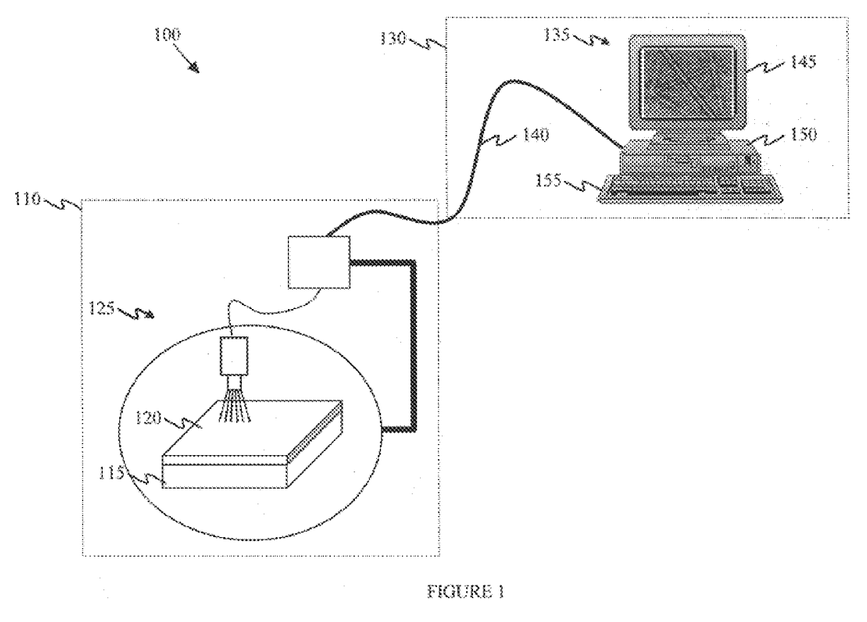
FIG. 1 illustrates a partial sectional view of an exemplary embodiment of a system for discerning two overlapping grain orientations, which may be used in accordance with the principals of the present invention.

Referring initially to FIG. 1, illustrated is a partial sectional view of an exemplary embodiment of a system 100 for discerning two overlapping grain orientations, which may be used in accordance with the principals of the present invention. It should initially be noted that the system 100 may include many objects, and is not be limited by what is illustrated in the embodiment shown in FIG. 1.

In the embodiment shown in FIG. 1, the system 100 includes a detection subsystem 110 and a comparison subsystem 130. The detection subsystem 110, in a preferred embodiment of the invention, may include a scanning electron microscope (SEM) 125. It should be noted, however, that the detection subsystem 110 may include other subsystems designed to detect grain orientations in a material 115 located on a substrate 120, including a transmission electron microscope (TEM), or a scanning transmission electron microscope (STEM), micro calorimetry, auger electron spectroscopy (AES), x-ray photoelectron spectroscopy (XPS) or a focused ion beam (FIB) process.

As previously mentioned, the system 100 may further include a comparison subsystem 130. The comparison subsystem 130 may include any subsystem capable of accurately comparing information obtained from the detection subsystem 110. In the embodiment illustrated in FIG. 1, the comparison subsystem 130 includes a computer subsystem 135. The computer subsystem 135 may be coupled to the detection subsystem 110 via a cable 140, and may be configured to receive and process information from the detection subsystem 110. In one embodiment of the present invention, the computer subsystem 135 may be software residing on a conventional personal computer. The software embodiment includes source code, object code, libraries, executable programs and other software structures that cooperatively function together to achieve the functionality of the present invention. The computer subsystem 135 may also include a monitor 145, a chassis 150 or a keyboard 155. Alternatively, however, the monitor 145 and the keyboard 155 may be replaced by other conventional output and input devices, respectively.

It should be noted that any conventional computer system having at least one CPU that is suitable to function as the computer subsystem 135, including without limitation, hand-held units, laptop/notebooks, minis, mainframes and supercomputers, including RISC and parallel processing architectures, as well as combinations of such systems, may be used. Conventional computer system architecture is more fully discussed in *Computer Organization and Architecture*, by William Stallings, MacMillan Publishing Co. (3rd ed. 1993), which is also incorporated herein by reference. Alternative computer system embodiments may be firm- or hardware-based. It should also be noted that the comparison subsystem 130 is not limited to an external source and may be included within a logic provided in the detection subsystem 110.

Figure 2:
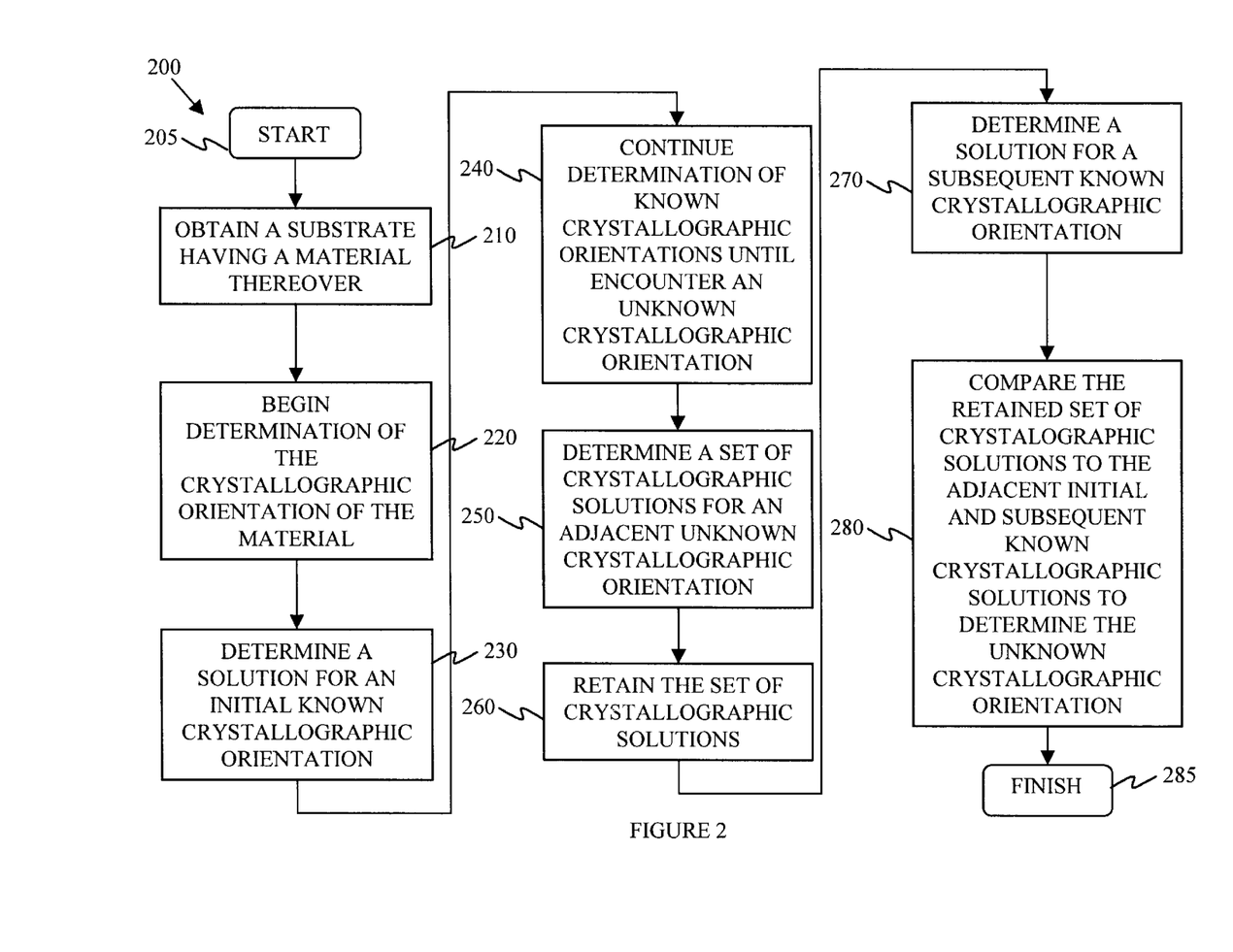
FIG. 2 illustrates a flow diagram of a method of determining a crystallographic quality of a material located on a substrate.

Turning now to FIG. 2, with continued reference to FIG. 1, illustrated is a flow diagram 200 of a method of determining a crystallographic quality of the material 120 located on the substrate 115. In FIG. 2, the method begins in a step 205. In a step 210, the substrate 115 having the material 120 thereon, may be obtained. The substrate 115 may comprise any substrate, and in a preferred embodiment, may be any layer located in a semiconductor device, including a layer located at wafer level or a layer located above or below wafer level. Furthermore, the material 120 may include many elements, and more specifically, it may include many elements typically used in the manufacture of a semiconductor device. Examples of such elements include, but are not limited to, copper, aluminum, titanium, titanium nitride, tungsten, tungsten silicide, tungsten salicide, cobalt silicide, tantalum nitride, and combinations thereof.

Subsequent to obtaining the substrate 115 having a material 120 thereover, in a step 220, determination of the crystallographic orientation of the material 120 may begin. To determine the crystallographic orientation of the material 120, the detection subsystem 110 preferably scans the surface of the material. In the preferred embodiment where the detection subsystem 110 includes the SEM 125, the SEM observes many points of the material 120 to determine the crystallographic orientation of such points.

Figure 3:
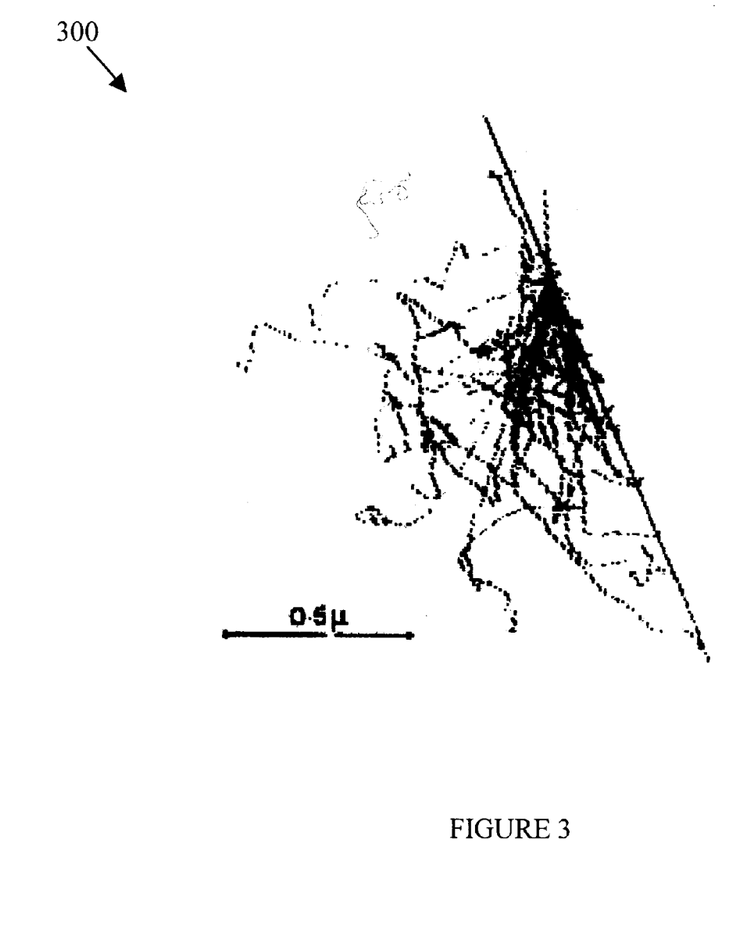
FIG. 3 illustrates a simulation of a 20 keV electron beam as it interacts with the material, which in the illustrative example, may be inclined at 70 degrees from normal.

Turning to FIG. 3, illustrated is a simulation 300 of a 20 keV electron beam as it interacts with the material 120, which in this illustrative example, may be inclined at 70 degrees from normal. As illustrated, this produces an interaction volume near the surface of the material, with electrons traveling in random directions. The directions that satisfy a Bragg angle may experience back reflection. Due to the point source nature of the electron beam interaction, planes satisfying the Bragg angle may diffract electrons falling on a cone whose axis is normal to the plane. With the effective wavelength and glancing angle variations from the electron source, a set of diffraction cones may exist for each group of planes within, creating a band structure visible on a phosphor screen. Such a visible band structure may be called a backscattered Kikuchi diffraction pattern.

Figure 4:
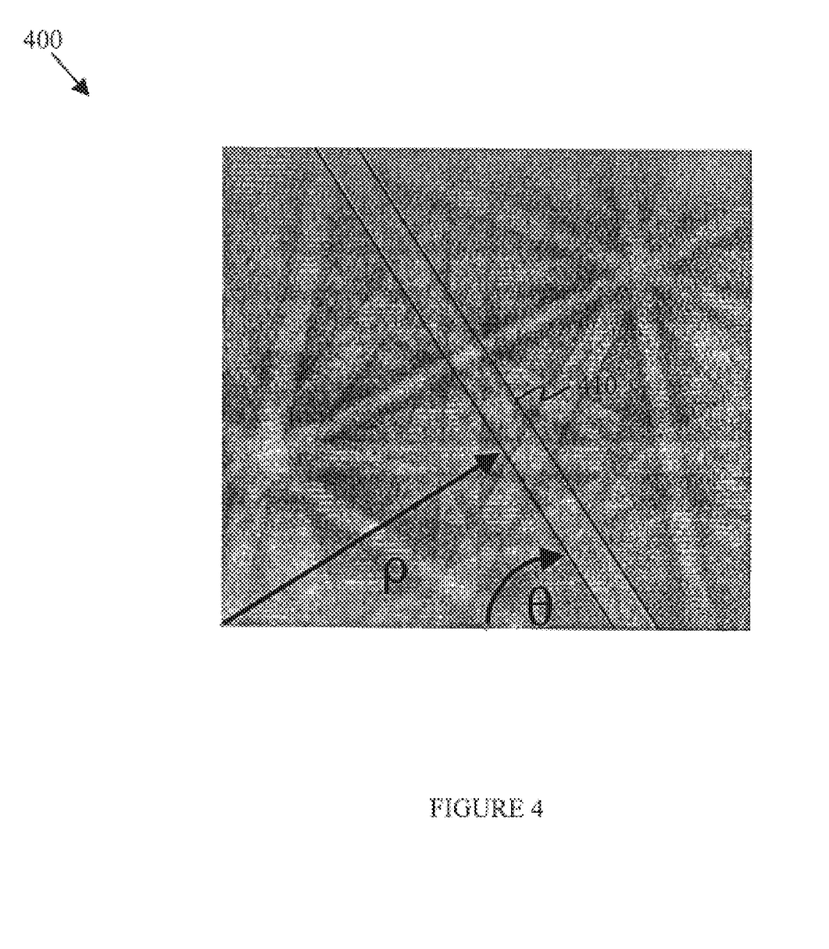
FIG. 4 illustrates one embodiment of such a visible band structure.

Turning briefly to FIG. 4, illustrated is one embodiment of such a visible band structure 400. As may be noticed, the visible band structure 400 includes a multitude of bands 410. The geometric arrangement of the bands 410 is a function of the phase and crystallographic orientation of the crystal lattice within the diffracting volume.

After determination of the visible band structure 400 for a given diffracting volume, which represents one observed point of the material 120, an advanced image analysis technique known as the Hough transform may be conducted. The Hough transform is used to transform the visible band structure 400, and more specifically the bands 410, to peaks of intensity representing each band 410.

Figure 5:
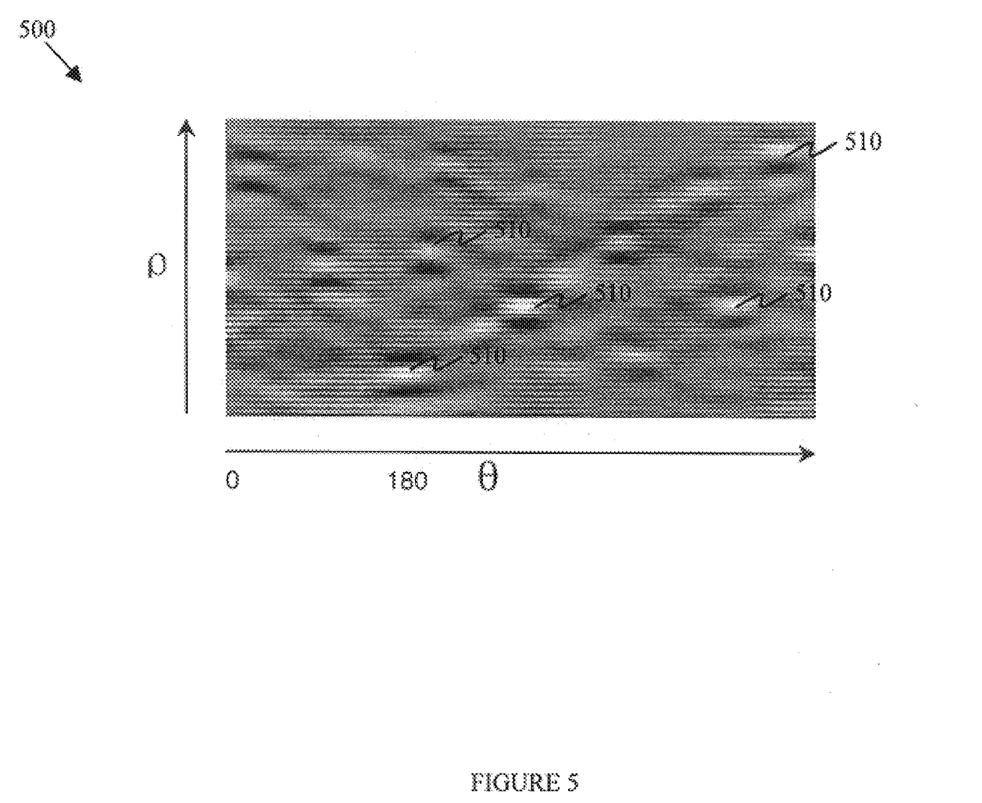
FIG. 5 illustrates a Hough transform of the visible band structure illustrated in FIG. 4.

Turning to FIG. 5, with continued reference to FIG. 4, illustrated is a Hough transform 500 of the visible band structure 400 illustrated in FIG. 4. As can be noticed, peaks of intensity 510 are located within the Hough transform 500. The Hough transform 500 may be determined by defining a Hough space, using the parameters ρ and θ derived from the visible band structure 400. Typically, ρ=x cos θ+y sin θ, where θ is the angle from the pattern axis. In a preferred embodiment, a first peak of intensity 510 may be determined, and additional peaks of intensity 510 may be determined by translating along a given axis in the space. Each peak of intensity 510 tends to correspond to one band 410, and the darker regions above and below each peak of intensity 510 tend to correspond to the darker regions on either side of the bands 410. In an exemplary embodiment, the thickness of the peak of intensity 510 is a function of interatomic plane spacing. Since the Hough transform has been conducted, the problem of finding the bands 410 in the visible band structure 400 is reduced to finding the point of intensity 510 in the Hough transform 500.

Referring back to FIG. 2, with continued reference to FIGS. 4 and 5, a solution for an initial known crystallographic orientation may be determined in a step 230. In the step 230, the points of intensity 510 in the Hough transform 500 may be used to determine the initial known crystallographic orientation. For example, a convolution mask may be performed to determine which peaks are most likely bands representing the crystallographic orientation of the initial observed point. In such an instance, the intensity difference between the brightness of the center of the points of intensity 510 and the dark regions above and below the brightness, may be used to choose which points of intensity 510 are the most likely points of intensity 510 representing the initial crystallographic orientation. The points of intensity 510 chosen to represent the initial crystallographic orientation may then be transformed back to bands, wherein the bands, using known rules of symmetry, may then be used to determine the solution for the initial known crystallographic orientation. In an exemplary embodiment of the invention, the computer subsystem 135 (FIG. 1), may be used to determine the solution for the initial known crystallographic orientation.

In the illustrative embodiment, once the points of intensity 510 chosen to represent the initial crystallographic orientation are transformed back to bands, a voting scheme may be used to actually determine the initial crystallographic orientation to within a high confidence index. In such an example, a look-up table of interplanar angles may be formed. Only the planes which may possibly be observed in the diffraction patterns, are included in the calculation of the look-up table. For example, in face-centered cubic aluminum, only the planes {111}, {200}, {220} and {311} are included. By considering all possible combinations of the possible planes and their symmetric equivalents, the look-up table of the possible unique interplanar angles may be generated (in the face-centered cubic aluminum example, the table would have 21 entries). Next, all possible sets of three bands are formed from the detected bands. The angles between the bands for each combination may be compared to the previously determined look-up table. From this comparison, Miller indices (hkl) associated with the bands may then be identified. If only one solution is found, the crystallographic orientation has been determined within a high confidence index.

Figure 6:
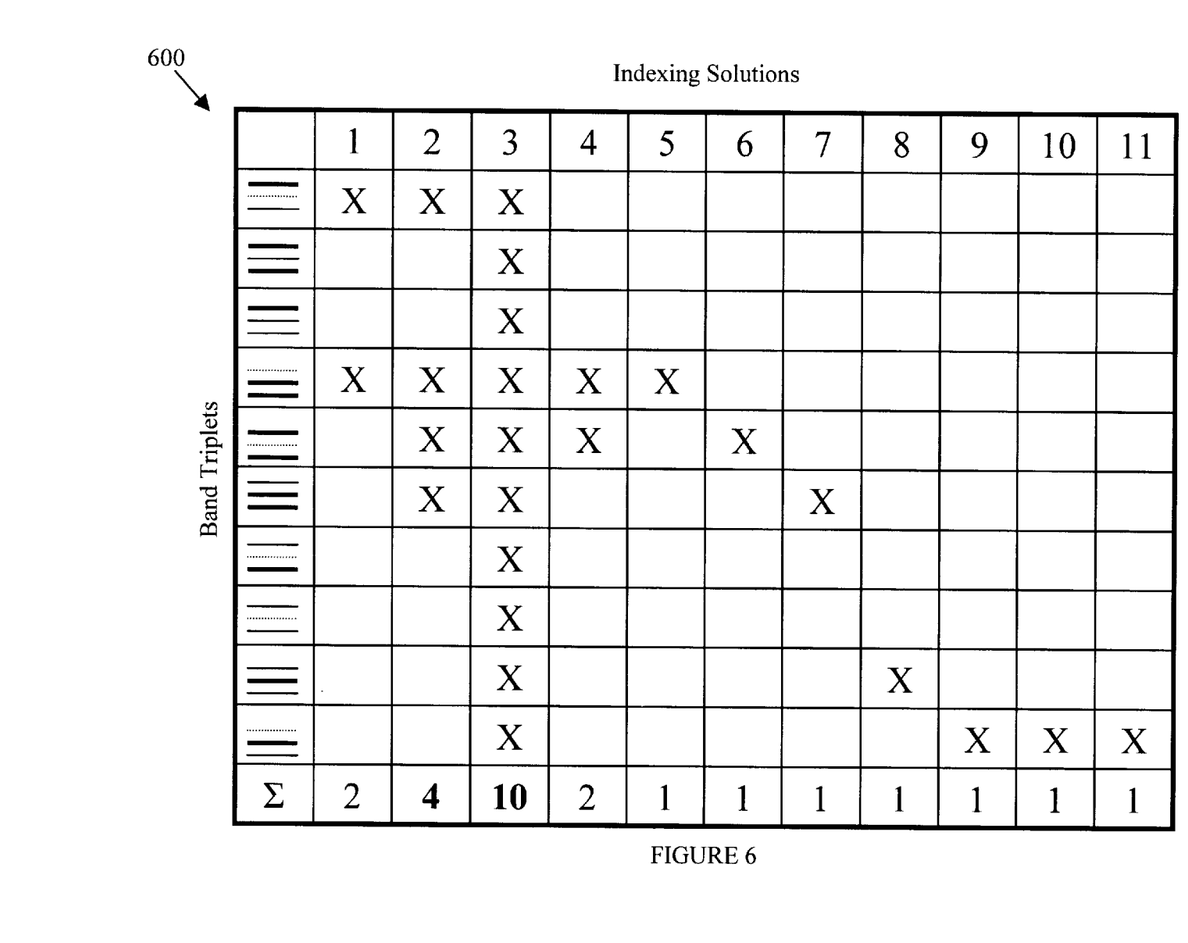
FIG. 6 illustrates a table showing a partial portion of the voting procedure and indexing results.

Often, however, more than one possible solution may be found for a triplet. The solutions found for all of the triplets may then be used in a voting scheme to identify the most probable indexing of the pattern, and determine a rank of crystallographic solutions. Turning to FIG. 6, an example of a table 600 showing a partial portion of the voting procedure and indexing results, is illustrated. The voting scheme may be used to calculate a confidence index for the various solutions. The confidence index for a given solution may be obtained by subtracting the votes associated with the solution which received the second highest number of votes from the solution with the most votes. This quantity may then be divided by the total possible number of band triplets that may be formed from the bands detected by the Hough transform. The confidence index ranges in value from zero to one, with a high confidence index being represented by a value of at least about 0.1 (95% confidence), and even more preferably, a value of at least about 0.3. In the example illustrated in FIG. 6, solution 3 has a confidence index of about 0.6. In the above illustrated example, a solution for the initial crystallographic orientation, within a high confidence index, has been obtained. Such an example might be an illustration where the electron beam encounters only one superimposed grain structure, such as in the middle of a grain. The voting scheme may also be used to calculate a "fit" parameter, which defines the average angular deviation between recalculated bands and the detected bands. Such recalculated bands indicate where the bands should appear based on the orientation obtained from the voting procedure.

After determining the solution for the initial known crystallographic orientation, the process could continue in a step 240, moving from point to point across the surface of the material 120 (FIG. 1), until encountering an adjacent unknown crystallographic orientation. The adjacent unknown crystallographic orientation could represent where the electron beam encounters multiple superimposed grain structures, such as what might be encountered at a grain boundary. After encountering the adjacent unknown crystallographic orientation, in a step 250, a set of crystallographic solutions for the adjacent unknown crystallographic orientation should be determined. If one solution for the adjacent unknown crystallographic orientation can not be selected within the high confidence index, in a step 260, the set of solutions should be retained without making a determination of which solution is correct. It should be noted that the step of retaining the solutions is in contrast to that taught in the prior art. It should also be noted that in an exemplary embodiment, the set of solutions may be retained within the computer system 135 (FIG. 1).

Subsequent to retaining the set of unknown crystallographic solutions, in a step 270, a solution for a subsequent known crystallographic orientation should be determined, the subsequent known crystallographic orientation preferably being adjacent the unknown crystallographic orientation. The determination of the solution for the subsequent known crystallographic orientation is similar to the determination of the initial known crystallographic orientation illustrated in step 230.

After determining the solution for the subsequent known crystallographic orientation, in a step 280, the retained set of crystallographic solutions may be compared to the adjacent initial and subsequent known crystallographic solutions, to determine the unknown crystallographic solutions. It should be noted that this may be accomplished either in real time, or in an alternative embodiment off-line. In such an example, the adjacent initial and subsequent known crystallographic solutions, each having the high confidence index, could be compared to the retained set of solutions having a lower confidence index.

Figure 7:
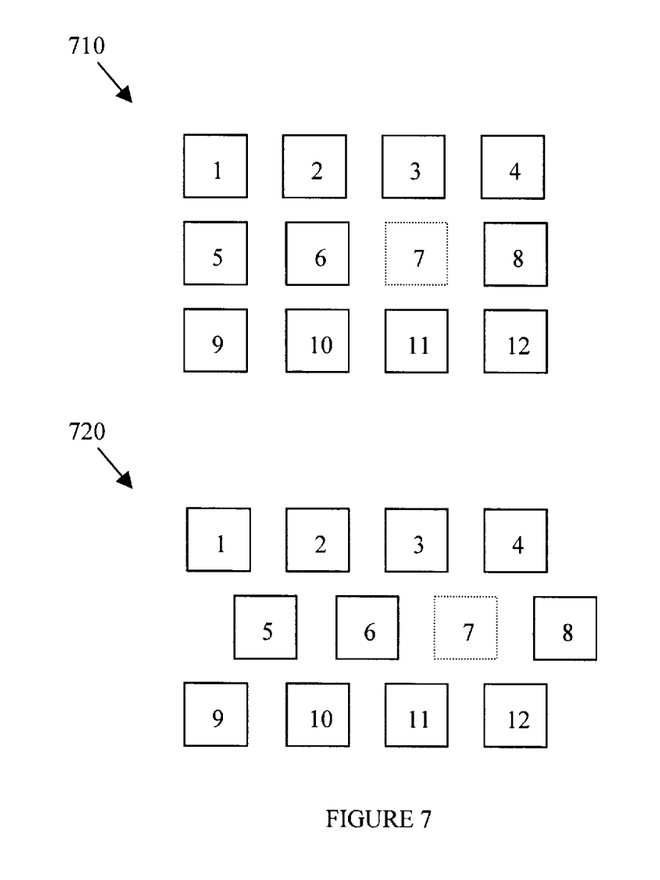
FIG. 7 illustrates a semiconductor device, which might be manufactured using the method of determining a crystallographic quality of a material, mentioned above.

In one example, the adjacent initial and subsequent known crystallographic solutions could be compared to the retained set of solutions having the lower confidence index. Generally the point to point nature of the stepping pattern occurs in a square 710 or hexagonal fashion 720, as illustrated in FIG. 7. If, for example, the point labeled 7 were the unknown crystallographic solution from which the solutions were retained, those solutions having a confidence index lower than a specified value, for example 0.15, would automatically be discarded. The remaining solutions having a confidence index over the specified value, would then be compared to the adjacent initial and subsequent known crystallographic solutions. In the square pattern 710 the adjacent initial and subsequent known crystallographic solutions would comprise points 2, 3, 4, 6, 8, 10, 11, and 12. Likewise, in the hexagonal pattern 720 the adjacent initial and subsequent known crystallographic solutions would comprise points 3, 4, 6, 8, 11, and 12. If any of the remaining solutions having a confidence index over the specified value were to have the same crystallographic orientation as any of the adjacent initial and subsequent known crystallographic solutions, the previously unknown crystallographic orientation would assume the crystallographic orientation of the matching adjacent initial and subsequent known crystallographic solution.

After determining the unknown crystallographic orientation, the process would continue scanning the surface of the material 120 (FIG. 1) using the previously mentioned steps 210 through 280. Depending on the speed of the process and number of available work cycles, this could occur after the process is completed. The process would subsequently finish in a step 285, preferably after scanning a large enough area of the material 120 to provide statistical relevance.

As a result of the above-mentioned method of determining a crystallographic quality of the material 120 located on the substrate 115, a determination of crystallographic orientations at grain boundaries may more accurately be accomplished. Moreover, the crystallographic orientations at grain boundaries may be accomplished without the guesswork, averaging and reconstruction typically associated with the prior art processes.

Figure 8:
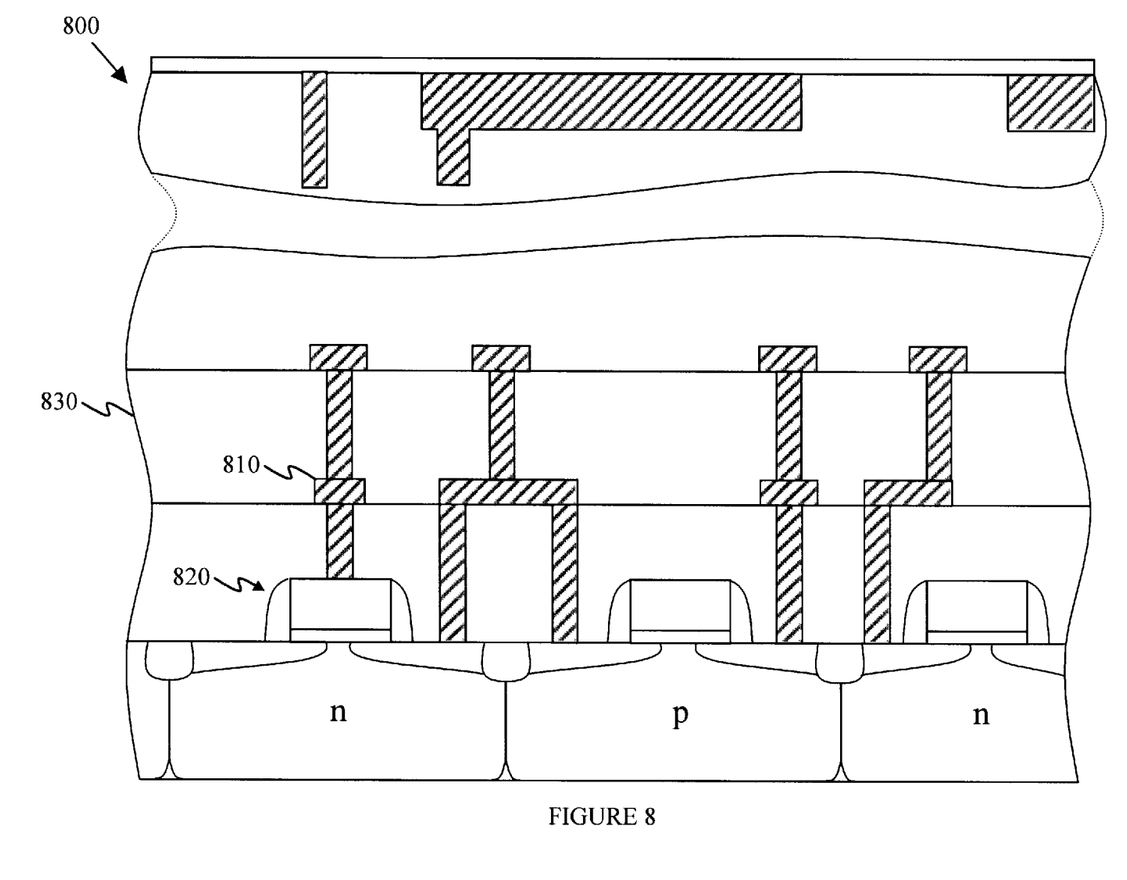

Turning to FIG. 8, illustrated is a semiconductor device 800, which might be manufactured using the method of determining a crystallographic quality of a material mentioned above. The method of determining a crystallographic quality of a material could be used to determine the crystallographic quality of any semiconductor structure being comprised of a material having a crystallographic quality. In the embodiment shown in FIG. 8, the semiconductor structure could be an interconnect 810, a transistor 820, an interlevel dielectric 830, or other similar structure.

Although the present invention has been described in detail, those skilled in the art should understand that they can make various changes, substitutions and alterations herein without departing from the spirit and scope of the invention in its broadest form.

What is claimed is:

1. A method of determining a crystallographic quality of a material located on a substrate, comprising:
    determining a set of crystallographic solutions for an unknown crystallographic orientation; and
    comparing the set of crystallographic solutions to adjacent known crystallographic orientations to determine the unknown crystallographic orientation.

2. The method as recited in claim 1 wherein determining a set of crystallographic solutions includes determining a rank of crystallographic solutions representing the most probable crystallographic orientations.

3. The method as recited in claim 2 wherein determining a rank of crystallographic solutions includes determining a number or votes, a fit and a confidence index for the crystallographic solutions.

4. The method as recited in claim 1 wherein comparing the set of crystallographic solutions to adjacent known crystallographic orientations includes comparing the set of crystallographic solutions to adjacent known crystallographic orientations having a high confidence index.

5. The method as recited in claim 4 wherein comparing the set of crystallographic solutions to adjacent known crystallographic orientations having a high confidence index includes comparing the set of crystallographic solutions to adjacent known crystallographic orientations having a high confidence index of at least about 0.1 out of a scale from zero to one.

6. The method as recited in claim 5 wherein comparing the set of crystallographic solutions to adjacent known crystallographic orientations having a high confidence index of at least about 0.1 includes comparing the set of crystallographic solutions to adjacent known crystallographic orientations having a high confidence index of at least about 0.3.

7. The method as recited in claim 1 wherein determining a set of crystallographic solutions for an unknown crystallographic orientation, comprises:
    determining a solution for a first known crystallographic orientation; then
    determining and retaining the set of crystallographic solutions for the unknown crystallographic orientation; then
    determining a solution for a second known crystallographic orientation.

8. The method as recited in claim 1 wherein determining a set of crystallographic solutions, further comprises:
    locating a peak of greatest intensity in a space derived from a crystallographic orientation representing the unknown crystallographic orientation;
    translating along an axis of the space until additional intensity peaks are determined; and
    determining the set of crystallographic solutions by analyzing combinations of three intensity peaks.

9. The method as recited in claim 8 wherein locating a peak of greatest intensity includes determining Kikuchi diffraction patterns of the unknown crystallographic orientation and transforming the Kikuchi diffraction patterns to a Hough space having the peaks of greatest intensity.

10. The method as recited in claim 1 wherein determining a set of crystallographic solutions for an unknown crystallographic orientation includes determining a set of crystallographic solutions for an unknown crystallographic orientation included within a material selected from the group consisting of copper, aluminum, titanium, titanium nitride cobalt silicide, tantalum nitride, and combinations thereof.

11. A method of manufacturing a semiconductor device, comprising:
    forming a semiconductor structure on a substrate, the semiconductor structure being comprised of a material having a crystallographic quality; and
    determining a crystallographic quality of the material, including:
        determining a set of crystallographic solutions for an unknown crystallographic orientation; and
        comparing the set of crystallographic solutions to adjacent known crystallographic orientations to determine the unknown crystallographic orientation.

12. The method as recited in claim 11 wherein determining a set of crystallographic solutions includes determining a rank of crystallographic solutions representing the most probable crystallographic orientations.

13. The method as recited in claim 12 wherein determining a rank of crystallographic solutions includes determining a number or votes, a fit and a confidence index for the crystallographic solutions.

14. The method as recited in claim 11 wherein comparing the set of crystallographic solutions to adjacent known crystallographic orientations includes comparing the set of crystallographic solutions to adjacent known crystallographic orientations having a high confidence index.

15. The method as recited in claim 14 wherein comparing the set of crystallographic solutions to adjacent known crystallographic orientations having a high confidence index includes comparing the set of crystallographic solutions to adjacent known crystallographic orientations having a high confidence index of at least about 0.1 out of a scale from zero to one.

16. The method as recited in claim 15 wherein comparing the set of crystallographic solutions to adjacent known crystallographic orientations having a high confidence index of at least about 0.1 includes comparing the set of crystallographic solutions to adjacent known crystallographic orientations having a high confidence index of at least about 0.3.

17. The method as recited in claim 11 wherein determining a set of crystallographic solutions for an unknown crystallographic orientation, comprises:

determining a solution for a first known crystallographic orientation; then determining and retaining the set of crystallographic solutions for the unknown crystallographic orientation; then determining a solution for a second known crystallographic orientation.

18. The method as recited in claim 11 wherein determining a set of crystallographic solutions, further comprises:

locating a peak of greatest intensity in a space derived from a crystallographic orientation representing the unknown crystallographic orientation;

translating along an axis of the space until additional intensity peaks are determined; and determining the set of crystallographic solutions by analyzing combinations of three intensity peaks.

19. The method as recited in claim 18 wherein locating a peak of greatest intensity includes determining Kikuchi diffraction patterns of the unknown crystallographic orientation and transforming the Kikuchi diffraction patterns to a Hough space having the peaks of greatest intensity.

20. The method as recited in claim 11 wherein determining a set of crystallographic solutions for an unknown crystallographic orientation includes determining a set of crystallographic solutions for an unknown crystallographic orientation included within a material selected from the group consisting of copper, aluminum, titanium, titanium nitride cobalt silicide, tantalum nitride, and combinations thereof.

* * * * *